United States Patent [19]

Dereu et al.

[11] Patent Number: 4,618,669

[45] Date of Patent: Oct. 21, 1986

[54] S-(CARBAMOYL-PHENYLSELENYL) DERIVATIVES OF GLUTATHIONE AND OF AMINOMERCAPTOCARBOXYLIC ACIDS

[75] Inventors: Norbert Dereu, Frechen-Bachem; André Welter, Pulheim; Albrecht Wendel; Sigurd Leyck, both of Tübingen; Michael Parnham, Pulheim; Erich Graf, Kerpen; Helmut Sies, Neuss; Hans Betzing, Kerpen-Horrem; Hartmut Fischer, Cologne, all of Fed. Rep. of Germany

[73] Assignee: A. Nattermann & Cie GmbH, Cologne, Fed. Rep. of Germany

[21] Appl. No.: 744,920

[22] Filed: Jun. 14, 1985

[30] Foreign Application Priority Data

Jun. 22, 1984 [DE]  Fed. Rep. of Germany ....... 3422962
Nov. 29, 1984 [DE]  Fed. Rep. of Germany ....... 3443468

[51] Int. Cl.$^4$ ................... C07K 5/08; C07C 149/40; C07C 121/50
[52] U.S. Cl. ................... 530/331; 562/426; 560/9; 558/415
[58] Field of Search ........... 562/426; 560/9; 260/465 D

[56] References Cited

U.S. PATENT DOCUMENTS 4,352,799 10/1982 Renson et al. .............. 424/244
4,418,069 11/1983 Welter et al. ............... 424/269

OTHER PUBLICATIONS

"Methods of Enzymology", vol. 77, pp. 325-333, A. Wendel.
"Fundamental and Applied Toxicology" (3)9-10/83, C. Channa Reddy and Edward J. Massaro.
"Free Radicals in Biology", vol. V, pp. 223 to 254, Leopold Flohe.
"Agents and Actions", Supp. 7, pp. 214-219, P. C. Bragt et al.

Primary Examiner—Delbert R. Phillips
Attorney, Agent, or Firm—Pearne, Gordon, Sessions, McCoy, Granger, & Tilberry

[57] ABSTRACT

The present invention relates to new S-(carbamoyl-phenylselenyl) derivatives of glutathione and of α-aminomercaptocarboxylic acids of the general formula (I)

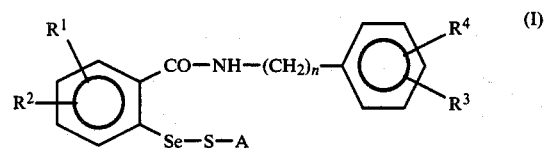

3 Claims, No Drawings

S-(CARBAMOYL-PHENYLSELENYL) DERIVATIVES OF GLUTATHIONE AND OF AMINOMERCAPTOCARBOXYLIC ACIDS

The present invention relates to new S-(carbamoyl-phenyl-selenyl) derivatives of glutathione and of α-aminomercapto-carboxylic acids, which are characterized by valuable pharmacological properties, and processes for their preparation and their use as active components in pharmaceutical compositions. They can be used in particular for the treatment of diseases caused by a cell injury due to increased formation of active oxygen metabolites, such as liver defects, cardiac infarction, inflammations, psoriasis, radiation defects.

The compounds of the present invention correspond to the general formula I

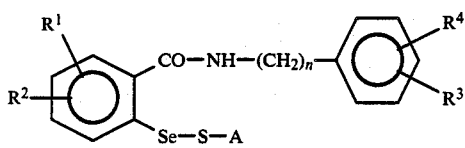

wherein $R^1$, $R^2$, $R^3$, $R^4$ which can be identical or different are independently hydrogen, halogen, $C_{1-4}$-alkyl, $C_{1-4}$-alkoxy, hydroxy, trifluoromethyl, nitro, cyano, carboxy, $C_{1-4}$-alkoxycarbonyl and n is zero or an integer from 1 to 4, while A represents the glutathione radical or an α-amino acid radical, wherein the carboxylic group can be esterified with an $C_{1-3}$-alcohol and the amino group can be acylated.

Halogen means fluorine, chlorine, bromine. As alkyl groups having 1 to 4 carbon atoms can be mentioned methyl, ethyl, propyl, isopropyl, butyl, isobutyl, sec-butyl, tert-butyl; as alkoxy groups having 1 to 4 carbon atoms can be mentioned methoxy, ethoxy, propoxy, butoxy.

Preferred are compounds wherein $R^1$, $R^2$, $R^3$, $R^4$, which are identical or different, each are independently hydrogen, fluorine, chlorine, methyl, methoxy, hydroxy, trifluoromethyl or nitro. Particularly preferred are compounds wherein $R^1$, $R^2$ are identical or different and independently hydrogen, fluorine, chlorine, methyl, methoxy, hydroxy, trifluoromethyl or nitro, while $R^3$, $R^4$ represent hydrogen or methoxy and A represents a L-glutathione or L-methionine radical.

The compounds of formula I exhibit a chirality center due to the α-positioned amino group in the respective amino acid test and can be present as racemate or in the form of the D- or L-enantiomers dependent on the kind of the used starting materials. If a separation of the racemates is desired, it is carried out conveniently using a process known per se with an optical active base through the formation of diastereomeric salts or by chromatography at an optical active column material.

Examples of compounds of the present invention are the following:
S-(2-phenylcarbamoyl-phenylselenyl)-L-glutathione
S-[2-(2-chlorphenylcarbamoyl)-phenylselenyl]-L-glutathione
S-[2-(3-fluorphenylcarbamoyl)-phenylselehyl]-L-glutathione
S-[2-(4-trifluormethylphenylcarbamoyl)-phenylselenyl]-L-glutathione
S-[2-(4-hydroxyphenylcarbamoyl)-phenylselenyl]-L-glutathione
S-[2-(4-methoxyphenylcarbamoyl)-phenylselenyl]-L-glutathione
S-[2-(3,4-dichlorphenylcarbamoyl)-phenylselenyl]-L-glutathione
S-(2-phenylcarbamoyl-5-methoxy-phenylselenyl)-L-glutathione
S-(2-phenylcarbamoyl-5-chlor-phenylselenyl)-L-glutathione
S-(2-phenylcarbamoyl-5-fluor-phenylselenyl)-L-glutathione
S-(2-phenylcarbamoyl-6-methoxy-phenylselenyl]-L-glutathione
S-[2-(4-nitrophenylcarbamoyl)-phenylselenyl]-L-glutathione
S-[2-(4-chlorophenylcarbamoyl)-phenylselenyl]-L-glutathione
S-[2-(4-flourophenylcarbamoyl)-6-methoxy-phenylselenyl)-L-glutathione
S-[2-(4-chlorophenylcarbamoyl)-6-methoxy-phenylselenyl]-L-glutathione
S-[2-(4-methylphenylcarbamoyl)-6-methoxy-phenylselenyl]-L-glutathione
S-[2-(3chlorophenylcarbamoyl)-6-methoxy-phenylselenyl]-L-glutathione
S-[2-(3-methoxyphenylcarbamoyl)-6-methoxy-phenylselenyl]-L-glutathione
S-[2-(3,4-dichlorophenylcarbamoyl)-6-methoxy-phenylselenyl]-L-glutathione
S-[2-(3,4-dichlorophenylcarbamoyl)-6-methoxy-phenylselenyl]-L-glutathione
S-[2-(3-flouro-4-methyl-phenylcarbamoyl)-6-methoxy-phenyl-selenyl]-L-glutathione
S-[2-(3-chloro-4-methoxy-phenylcarbamoyl)-6-methoxy-phenylselenyl]-L-glutathione
S-[2-(3,4-dimethoxyphenylcarbamoyl)-6-methoxy-phenylselenyl]-L-glutathione
S-[2-(2-methoxy-4-nitro-phenylcarbamoyl)-6-methoxy-phenylselenyl]-L-glutathione
S-(2-phenylcarbamoyl-phenylselenyl)-L-cysteine
S-(2-phenylcarbamoyl-6-methoxy-phenylselenyl)-L-cysteine
S-[2-(4-carboxyphenylcarbamoyl)-phenylselenyl]-L-cysteine
S-[2-(4-ethoxycarbonylphenylcarbamoyl)-phenylselenyl]-L-cysteine
S-[2-(4-cyanphenylcarbamoyl)-phenylselenyl]-L-cysteine
S-(2-benzylcarbamoyl-phenylselenyl)-L-cysteine
S-[2-(4-phenylbutylcarbamoyl)-phenylselenyl]-L-cysteine
S-(2-phenylcarbamoyl-phenylselenyl)-L-cysteinmethylester
S-(2-phenylcarbamoyl-phenylselenyl)-L-cysteinethylester
S-(2-phenylcarbamoyl-phenylselenyl)-L-cysteinpropylester
S-[2-(4-trifluoromethylphenylcarbamoyl)-phenyl-selenyl)-L-cysteinmethylester
S-(2-phenylcarbamoyl-phenylselenyl)-N-acetyl-L-cysteine
S-[2-(2-chlorophenylcarbamoyl)-phenylselenyl]-N-acetyl-L-cysteine
S-[2-(4-methoxyphenylcarbamoyl)-phenylselenyl]-N-acetyl-L-cysteine
S-[3-(4-fluorophenylcarbamoyl)-phenylselenyl]-N-acetyl-L-cysteine S-[2-(4-fluorophenylcarbamoyl)-6-methoxy-phenyl-selenyl]-N-acetyl-L-cysteinmethylester
S-(2-phenylcarbamoyl phenylselenyl)-DL-homocysteine
S-(2-phenylcarbamoyl-6-methoxy-phenylselenyl)-DL-homocysteine
S-[2-(4-carboxyphenylcarbamoyl)-phenylselenyl]-DL-homocysteine
S-[2-(4-methoxycabonylphenylcarbamoyl)-phenyl-selenyl]-DL-homocysteine
S-[2-(4-cyanphenylcarbamoyl)-phenylselenyl]-DL-homocysteine
S-(2-benzylcarbamoyl-phenylselenyl)-DL-homocysteine
S-[2-(4-phenylbutylcarbamoyl)-phenylselenyl]-DL-homocysteine
S-(2-phenylcarbamoyl-phenylselenyl)-DL-homocysteinethylester
S-(2-phenylcarbamoyl-phenylselenyl)-N-acetyl-DL-homocysteine
S-(2-phenylcarbamoyl-6-methoxy-phenylselenyl)-N-acetyl-DL-homocysteine
S-(2-phenylcarbamoyl-phenylselenyl)-N-acetyl-DL-homocysteinmethylester
S-(2-phenylcarbamoyl-phenylselenyl)-D-penicillamine
S-(2-phenylcarbamoyl-6-methoxy-phenylselenyl)-D-penicillamine
S-[2-(4-carboxyphenylcarbamoyl)-phenylselenyl]-D-penicillamine
S-[2-(4-ethoxycarbonylphenylcarbamoyl)-phenyl-selenyl]-D-penicillamine
S-[2-(4-cyanphenylcarbamoyl)-phenylselenyl]-D-penicillamine
S-(2-benzylcarbamoyl-phenylselenyl)-D-penicillamine
S-[2-(4-phenylbutylcarbamoyl)-phenylselenyl]-D-penicillamine
S-(2-phenylcarbamoyl-phenylselenyl)-D-penicillaminmethylester
S-(2-phenylcarbamoyl-6-methoxy-phenylselenyl)-D-penicillaminmethylester
S-(2-phenylcarbamoyl-phenylselenyl)-N-acetyl-D-penicillamine
S-(2-phenylcarbamoyl-6-methoxy-phenylselenyl)-N-acetyl-D-penicillamine
S-(2-phenylcarbamoyl-phenylselenyl)-N-acetyl-D-penicillaminmethylester The substances of the present invention exhibit glutathione peroxidase-like properties and are capable to replace this enzyme and to prevent in this way in cooperation with a mercaptane the harmful effects of active oxygen metabolites.

The selenium dependent glutathione (GSH)-peroxidase (Px) catalyses the reduction of $H_2O_2$ and of organic hydroperoxides:

$$2 \text{ GSH} + H_2O_2 \xrightarrow{\text{GSH—Px}} \text{GSSG}$$

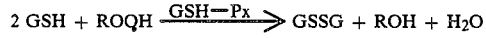

$$2 \text{ GSH} + \text{ROQH} \xrightarrow{\text{GSH—Px}} \text{GSSG} + \text{ROH} + H_2O$$

The selenium containing enzyme protects the cells against the peroxidation and plays an important role in the modulation of the arachidonic acid metabolism (C. C. Reddy, E. J. Massaro, Fundam. and Appl. Toxicology (3), 9–10 (1983), pages 431–436, and L. Flohé, Free Radicals in Biology, vol. V, edited by W. A. Pryor 1982 Academic Press, pages 223–254).

The glutathione peroxidase plays a role in all diseases wherein a cell injury of the respective tissue and finally a necrose results due to an increased formation of active oxygen metabolites in form of peroxides (such as lipoid peroxide and hydrogen peroxide). This so-called "oxidative stress" can for example be seen in liver diseases—induced by inflammative or autoimmunologic reactions, by alcohol or by medicaments—but also in other diseases, for example cardiac infarctions. It is known, that after a cardiac infarction, leucocytes migrate into the injured area and that the cell destruction is accompanied by an increased releasing of the above named active oxygen metabolites. Finally, this leads to a progressive decomposition of the tissue.

In such cases, the important and naturally existing protecting system consisting of various peroxides and active oxygen decompositing enzymes is overloaded. This includes superoxide dismutase, catalase, and particularly the glutathione redox system with the respective enzyme component glutathione peroxidase. The latter principal is of a great importance, since it is capable to depoison both organic peroxides and hydrogen peroxide. It is confirmed that this system plays an important role for the intact liver function (Wendel et al., Biochemical Pharmacology, vol. 31, page 3601 (1982)) and that for example the extent of an experimental liver injury is dependent on this system, i.e. on the content of the liver of glutathione on one side and on the activity of the enzyme glutathione peroxidase on the other side. In the course of a generic inflammation, this liver protection mechanism is essentially reduced (Bragt et al., Agents and Actions, Supp. 7, page 214 (1980), so that the liver suffers from an essentially increased "oxidative stress".

A very important role is played by the reactive oxygen metabolites as mediators of inflammations. They seem to cooperate in leucotaxis, vessel permeability, injuries of connective tissue and immunocomplex/complement-induced effects as well as in injuries caused by reflowing into ischemic areas (L. Flohé et al., The Pharmacology of Inflammation, ed. I. L. Bonta et al., Handbook of Inflammation, vol. 5, Elsevier, Amsterdam, pages 255–270).

Also the injuries after ionizing radiation are caused by the formation of radicals and of active oxygen metabolites. Another route for the chemical cytoprotection is the strengthening of the glutathione/glutathioneperoxidase system.

The measuring of the glutathione peroxidase-like activity is carried out by the method of A. Wendel (A. Wendel, Methods in Enzymology, vol. 77, 325–333 (1981)). In this experiment, the reaction of the co-substrate nicotine amide-adenin-dinucleotide-phosphate is measured. The reducing agent in this case is not glutathione, but the mercaptane containing aminoacid which has been used for the synthesis of the respective compounds. Surprisingly, now it has been found that the compounds of the present invention of formula I possess a glutathione peroxidase-like activity. The reaction of the benzoisoselenazolone with mercaptane containing amino acids follows in the example of 2-phenyl-1,2-benzoisoselenazol-3-(2H)-one according to the following equation:

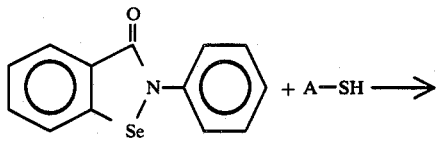

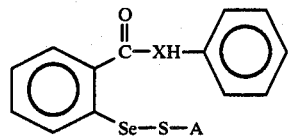

A = amino acid radical.

Glutathione-peroxidase-like activity

In in vitro-experiments, the catalysis of the peroxidase destruction has been examined. It was found, that the compounds of the present invention can replace the glutathioneperoxidase.

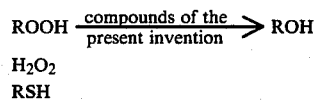

The reaction rates were measured by the method of A. Wendel (A. Wendel, Methods in Enzymology, vol. 77, pages 325–333 (1981)). As a reference substance, S-(2-phenylcarbamoyl-phenylselenyl) glutathione was used. In the presence of a 1 millimolar concentration of glutathione with tert-butylhydroperoxide a reaction rate of $1{,}17 \times 10^6$ units per mol is obtained. This activity is taken as 100% for comparative purposes.

| | catalytic activity (%) |
|---|---|
| S—(2-phenylcarbamoyl-phenylselenyl)-L—glutathione | 100 |
| S—[2-(2-chlorophenylcarbamoyl)-phenylselenyl]-L—glutathione | 39 |
| S—[2-(2-methoxyphenylcarbamoyl)-phenylselenyl]-L—glutathione | 37 |
| S—[2-(3-fluorophenylcarbamoyl)-phenylselenyl]-L—glutathione | 113 |
| S—[2-(4-trifluoromethylphenylcarbamoyl)-phenylselenyl]-L—glutathione | 49 |
| S—[2-(4-methoxyphenylcarbamoyl)-phenylselenyl]-L—glutathione | 124 |
| S—[2-(3,4-dichlorophenylcarbamoyl)-phenylselenyl]-L—glutathione | 21 |
| S—(2-phenylcarbamoyl-5-methoxy-phenylselenyl)-L—glutathione | 63 |
| S—(2-phenylcarbamoyl-5-chlor-phenylselenyl)-L—glutathione | 99 |
| S—(2-phenylcarbamoyl-5-fluor-phenylselenyl)-L—glutathione | 92 |
| S—(2-phenylcarbamoyl-6-methoxy-phenylselenyl)-L—glutathione | 225 |
| S—[2-(4-nitrophenylcarbamoyl)-phenylselenyl]-L—glutathione | 121 |
| S—[2-(4-chlorophenylcarbamoyl)-phenylselenyl]-L—glutathione | 116 |
| S—(2-phenylcarbamoyl-phenylselenyl)-L—cysteine | 210 |
| S—(2-phenylcarbamoyl-phenylselenyl)-N—acetyl-L—cysteine | 40 |
| S—(2-phenylcarbamoyl-phenylselenyl)-D—penicillamine | 25 |
| S—(2-benzylcarbamoyl-phenylselenyl)-L—cysteine | 56 |
| S—[2-(4-fluorophenylcarbamoyl)-phenylselenyl]-N—acetyl-L—cysteine | 61 |
| S—(2-phenylcarbamoyl-6-methoxy-phenylselenyl)-L—cysteine | 440 |

The preparation of the compounds of the present invention is carried out by reacting 1,2-benzoisoselenazolines of the formula II obtained as prescribed in DE-OS No. 30 27 073=U.S. Pat. No. 4,352,799 and DE-OS No. 30 27 075=U.S. Pat. No. 4,418,069 respectively, with glutathione and with α-aminomercaptocarboxylic acids or derivatives thereof, respectively:

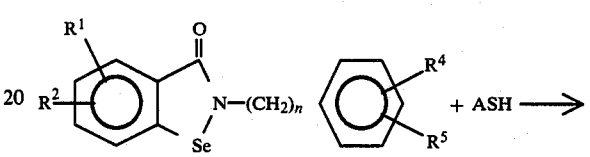

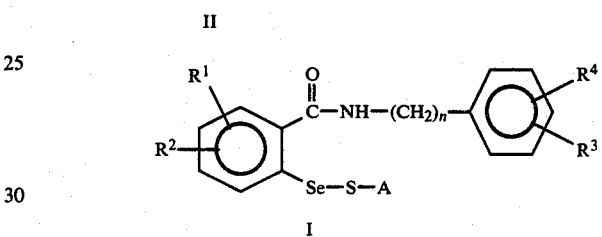

The reaction is carried out while stirring at room temperature in water and in solvents miscible with water, respectively. The α-amino mercaptocarboxylic acids and glutathione, respectively, used for the reaction, are known substances.

The present invention relates in addition to pharmaceutical preparations containing compounds of formula I. The pharmaceutical preparations of the present invention are suited for the enteral administration, such as oral or rectal administration, as well as for the parenteral administration, and they contain the pharmaceutical active components alone or together with a common pharmaceutical acceptable carrier. Preferably, the pharmaceutical composition of the active component has the form of single doses which can be adapted to the desired route of administration, such as tablets, dragees, capsules, suppositories, granules, solutions, emulsions or suspensions. The dosage of the substances ordinarily lies within the range from 10 to 1000 mg per day, preferably between 30 and 300 mg per day, and can be administered in a single dose or in several part doses, preferably in two to three part doses per day.

The preparation of the compounds of the present invention is illustrated in detail in the following examples. The melting points indicated therein were measured using a Büchi 510-melting point measurement apparatus and are indicated in centigrade and not corrected.

EXAMPLE 1

S-(2-Phenylcarbamoyl-phenylselenyl)-L-glutathione 1,1 g L-glutathione (4 mmol) are dissolved in 20 ml water. A solution of 1 g 2-phenyl-1,2-benzoisoselenazol-3(2H)-one (3,65 mmol) in 10 ml dimethylformamide is added slowly while stirring. The solution which is at first turbid, after completion of the addition becomes clear and yellow. Some minutes later, a precipitate appears. The suspension is stirred during the night. The precipitate is sucked off, washed with 50 ml water, then with 20 ml ethanol and dried.

Yield: 1,95 g (92,8% of the theory), melting point (Fp.) 245°–247° (decomposition).

| Analysis | calculated | found |
|---|---|---|
| C | 47,5% | 47,49% |
| H | 4,5% | 4,53% |
| N | 9,6% | 9,48% |
| S | 5,5% | 6,07% |
| Se | 13,6% | 14,40% |

In a $^{77}$Se NMR spectrum, a signal at 959 ppm (reference $CH_3$-Se-$CH_3$) for 2-phenyl-1,2-benzoisoselenazole-3(2H)-one can be seen. This signal is no more contained in the reaction product. However, a new signal at 394 ppm appears. This chemical shift is characteristic for selenylsulfides.

EXAMPLE 2

S-[2-(4-Methoxyphenylcarbamoyl)-phenylselenyl]-L-glutathione

Similar to example 1, 1,1 g L-glutathione (4,0 mmol) in 20 ml water are treated with a solution of 1,1 g 2-(4-methoxyphenyl)-1,2-benzoisoselenazole-3(2H)-one (3,62 mmol) in 10 ml dimethylformamide. The precipitate is stirred during the night and sucked off, washed with 50 ml water, then with 20 ml ethanol and dried.

Yield: 1,5 g (67,7% of the theory), Fp. 238°–243° C.

| Analysis | calculated | found |
|---|---|---|
| Se | 12,9% | 13,4% |

EXAMPLE 3

S-[2-(4-Chlorophenylcarbamoyl)-phenylselenyl]-L-glutathione

Similar to example 1, 1,1 g L-glutathione (4,0 mmol) in 20 ml water are treated with a solution of 1,2 g 2-(4-chlorophenyl)-1,2-benzoisoselenazole-3(2H)-one in 10 ml dimethylformamide. After the usual procedures, 1,1 g (45,9% of the theory), Fp. 279°–283° C., are obtained.

| Analysis | calculated | found |
|---|---|---|
| Se | 12,8% | 12,9% |

EXAMPLE 4

S-[2-(methoxyphenylcarbamoyl)-phenylselenyl]-L-glutathione

It is obtained similar to example 1 from 1 g 2-(3-methoxyphenyl)-1,2-benzoisoselenazole-3(2H)-one (3,29 mmol).

Yield: 1,4 g (69,5% of the theory), Fp. 222°–225° C.

| Analysis | calculated | found |
|---|---|---|
| Se | 12,9% | 13,8% |

EXAMPLE 5

S-[2-(4-Cyanophenylcarbamoyl)-phenylselenyl]-L-glutathione

It is obtained similar to example 1 from 1,1 g 2-(4-cyanophenyl)-1,2-benzoisoselenazole-3(2H)-one (3,67 mmol).

Yield: 1,25 g (56,1% of the theory), Fp. 227°–235° C. (decomposition).

| Analysis | calculated | found |
|---|---|---|
| Se | 13,0% | 13,9% |

EXAMPLE 6

S-(2-Phenylcarbamoyl-5-fluoro-phenylselenyl)-L-glutathione

It is obtained similar to example 1 from 1,1 g 6-fluoro-2-phenyl-1,2-benzoisoselenazole-3(2H)-one (3,77 mmol).

Yield: 1,75 g (77,4% of the theory), Fp. 250°–270° C. (decomposition).

| Analysis | calculated | found |
|---|---|---|
| Se | 13,2% | 13,7% |

EXAMPLE 7

S-[2-(3,4-Dichlorophenylcarbamoyl)-phenylselenyl]-L-glutathione

It is obtained similar to example 1 from 1,0 g 2-(3,4-dichlorophenyl)-1,2-benzoisoselenazole-3(2H)-one (2,91 mmol).

Yield: 1,65 g (87% of the theory), Fp. 265°–271° C.

| Analysis | calculated | found |
|---|---|---|
| Se | 12,1% | 12,6% |

EXAMPLE 8

S-[2-(4-Chloro-3-methoxy-phenylcarbamoyl)-phenylselenyl]-L-glutathione

It is obtained similar to example 1 from 1,2 g 2-(4-chloro-3-methoxyphenyl)-1,2-benzoisoselenazole-3(2H)-one (3,54 mmol).

Yield: 1,7 g (74,3% of the theory), Fp. 240°–248° C. (decomposition).

| Analysis | calculated | found |
|---|---|---|
| Se | 12,2% | 12,5% |

EXAMPLE 9

S-(2-phenylcarbamoyl-6-methoxy-phenylselenyl)-L-glutathione

It is obtained similar to example 1 from 1,4 g 7-methoxy-2-phenyl-1,2-benzoisoselenazole-3(2H)-one (4,61 mmol).

Yield: 1,85 g (65,6% of the theory), Fp. 235°–241° C. (decomposition).

| Analysis | calculated | found |
| --- | --- | --- |
| Se | 12,9% | 12,8% |

EXAMPLE 10

S-[2-(3-fluorophenylcarbamoyl)-phenylselenyl]-L-glutathione

It is obtained similar to example 1 from 1,65 g 2-(3-fluorophenyl)-1,2-benzoisoselenazole-3(2H)-one (5,65 mmol).

Yield: 2,1 g (62% of the theory), Fp. 268°–274° C. (decomposition).

| Analysis | calculated | found |
| --- | --- | --- |
| Se | 13,2% | 12,9% |

EXAMPLE 11

S-(2-Phenylcarbamoyl-phenylselenyl)-L-cysteine 2,74 g (10 mmol) 2-phenyl-1,2-benzoisoselenazole-3(2H)-one and 1,21 g (10 mmol) L-cysteine are dissolved in 25 ml trifluororacetic acid. This solution is stirred for 18 hours at room temperature. Then, 150 ml of an ice-water mixture are added to this solution. The deposited precipitate after some stirring becomes solid. It is sucked off and finally dissolved in methanol. After evaporation of the solvent, a residue remains which is washed with ether.

Yield: 3,85 g (97,5% of the theory), Fp. 250° C. (decomposition).

EXAMPLE 12

S-(2-phenylcarbamoyl-phenylselenyl)-D-penicillamine 5 g (18,2 mmol) 2-phenyl-1,2-benzoisoselenazole-3-(2H)-one are dissolved in 250 ml methanol and 30 ml dimethylformamide. A solution of 2,71 g (18,2 mmol) D-penicillamine in 100 ml water is added while stirring. To this clear solution, so much water is added until a slight haze is to be seen. After stirring for 18 hours, the precipitate is filtered and recristallized from ethanol/water (3:2).

Yield: 6,1 g (79% of the theory), Fp. 265°–266° C.

| $[\alpha]^{20}Na_{589}$: | +67,5 |
| --- | --- |
| $Hg_{578}$: | +69,6 |

EXAMPLE 13

S-(2-Phenylcarbamoyl-phenylselenyl)-D,L-penicillamine

It is prepared similar to example 12.
Yield: 5,95 g (77,2% of the theory), Fp. 255°–256° C.

EXAMPLE 14

S-(2-Phenylcarbamoyl-phenylselenyl)-N-acetyl-L-cysteine

It is obtained similar to example 12 from : 1 g (3,65 mmol) 2-phenyl-1,2-benzoisoselenazole-3(2H)-one in 50 ml methanol and 6 ml dimethylformamide and 0,6 g (3,67 mmol) N-acetyl-L-cysteine in 20 ml water.

Yield: 0,95 g (60% of the theory), Fp. 167°–168° C.

EXAMPLE 15

S-(2-Phenylcarbamoyl-phenylselenyl)-L-cysteinethylester

It is obtained similar to example 11 from: 2,2 g (8 mmol) 2-phenyl-1,2-benzoisoselenazole-3(2H)-one and 1,2 g (8 mmol) L-cysteinethylester in 20 ml trifluoroacetic acid.

Yield: 2,2 g (65% of the theory), Fp. 230° C. (decomposition).

EXAMPLE 16

S-[2-(4-fluorophenylcarbamoyl)-phenylselenyl]-N-acetyl-L-cysteine

It is obtained similar to example 12 from: 1 g (3,42 mmol) 2-(4-fluorophenyl)-1,2-benzoisoselenazole-3(2H)-one in 50 ml methanol and 6 ml dimethylformamide and 0,6 g (3,67 mmol) N-acetyl-L-cysteine in 20 ml water.

Yield: 1,5 g (96% of the theory), Fp. 110° C.

EXAMPLE 17

S-[2-(4-Nitrophenylcarbamoyl)-phenylselenyl]-D-penicillamine

It is obtained similar to example 12 from: 1 g (3,13 mmol) 2-(4-nitrophenyl)-1,2-benzoisoselenazole-3(2H)-one in 50 ml methanol and 6 ml dimethylformamide and 0,5 g (3,35 mmol) D-penicillamine in 20 ml water.

Yield: 0,63 g (43% of the theory), Fp. 158° C. (decomposition).

EXAMPLE 18

S-(2-Phenylcarbamoyl-6-methoxy-phenylselenyl)-N-acetyl-L-cysteine

It is obtained similar to example 12 from: 1 g (3,29 mmol) 2-phenyl-7-methoxy-1,2-benzoisoselenazole-3(2H)-one in 50 ml methan 1 and 6 ml dimethylformamide and 0,55 g (3,37 mmol) N-acetyl-L-cysteine in 20 ml water.

Yield: 1,45 g (94,4% of the theory), Fp. 181° C.

EXAMPLE 19

S-(2-Phenylcarbamoyl-phenylselenyl)-DL-homocysteine

It is obtained similar to example 11 from: 2,74 g (10 mmol) 2-phenyl-1,2-benzoisoselenazole-3(2H)-one and 1,35 g (10 mmol) DL-homocysteine.

Yield: 3,70 g (90,5% of the theory), Fp. 270° C. (decomposition).

EXAMPLE 20

S-(2-Benzylcarbamoyl-phenylselenyl)-D-penicillamine

It is obtained similar to example 12 from: 2,88 g (10 mmol) 2-benzyl-1,2-benzoisoselenazole-3(2H)-one and 1,5 g (10 mmol) D-penicillamine.

Yield: 4,3 g (98,4% of the theory), Fp. 182° C.

EXAMPLE 21

S-(2-Benzylcarbamoyl-phenylselenyl)-L-cysteine

It is obtained similar to example 11 from: 2,88 g (10 mmol) 2-benzyl-1,2-benzoisoselenazole-3(2H)-one and 1,21 g (10 mmol) L-cysteine.

Yield: 4,0 g (97,8% of the theory), Fp. 192°–194° C.

EXAMPLE 22

S-(2-Benzylcarbamoyl-phenylselenyl)-L-cysteinethylester

It is obtained similar to example 11 from: 2,88 g (10 mmol) 2-benzyl-1,2-benzisoselenazole-3(2H)-one and 1,5 g (10 mmol) L-cysteinethylester.

Yield: 3,9 g (89% of the theory), Fp. 220° C. (decomposition).

What we claim is:

1. S-(Carbamoyl-phenylselenyl) derivatives of glutathione and of α-aminomercaptocarboxylic acids according to the general formula (I)

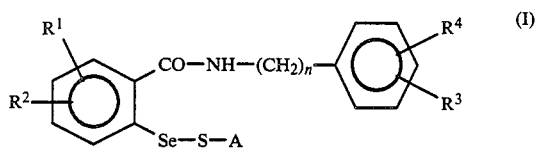

wherein $R^1$, $R^2$, $R^3$ and $R^4$, represent members selected from the group consisting of hydrogen, halogen, $C_{1-4}$-alkyl, $C_{1-4}$-alkoxy, trifluoromethyl, nitro, cyano, hydroxy, carboxy and $C_{1-4}$-alkoxycarbonyl, n is zero or an integer from 1 to 4 and A is a member selected from the group consisting of the glutathione radical, the α-amino acid radicals, the α-amino acid radicals wherein the carboxylic group and the amino group are unsubstituted the α-amino acid radicals wherein the carboxylic group is esterified with a $C_{1-3}$-alcohol and the amino group is unsubstituted, the α-amino acid radicals wherein the amino group is acylated and the carboxylic group is unsubstituted, and the α-amino acid radicals wherein both the carboxylic group is esterified with a $C_{1-3}$-alcohol and the amino group is acylate 2. S-(Carbamoyl-phenylselenyl) derivatives of L-glutathione according to formula (I) in claim 1, wherein $R^1$ and $R^2$ are members selected from the group consting of hydrogen, fluorine, chlorine, methyl, methoxy, hydroxy, .trifluoromethyl and nitro, $R^3$ and $R^4$ are members selected from the group consisting of hydrogen, fluorine, chlorine, methoxy and hydroxy, n is zero and A represents the L-glutathione radical.

3. S-(Carbamoyl-phenylselenyl) derivatives of L-cysteine according to formula (I) of claim 1, wherein $R^1$ and $R^2$ are members selected from the group consisting of hydrogen, fluorine, chlorine, methyl, methoxy, hydroxy, trifluoromethyl and nitro, $R^3$ and $R^4$ are members selected from the group consisting of hydrogen, fluorine, chlorine, methyl, methoxy and hydroxy, n is zero or an integer from 1 to 4 and A represents the L-cysteine radical.

* * * * *